(12) United States Patent
Desai

(10) Patent No.: US 7,200,495 B2
(45) Date of Patent: Apr. 3, 2007

(54) METHOD AND APPARATUS FOR ANALYZING SPATIAL AND TEMPORAL PROCESSES OF INTERACTION

(75) Inventor: Mukund N. Desai, Needham, MA (US)

(73) Assignee: The Charles Stark Draper Laboratory, Cambridge, MA (US)

(*) Notice: Subject to any disclaimer, the term of this patent is extended or adjusted under 35 U.S.C. 154(b) by 488 days.

(21) Appl. No.: 10/411,860

(22) Filed: Apr. 11, 2003

(65) Prior Publication Data

US 2003/0194815 A1 Oct. 16, 2003

Related U.S. Application Data

(60) Provisional application No. 60/371,913, filed on Apr. 11, 2002.

(51) Int. Cl.
*G01N 31/00* (2006.01)
*G01N 15/06* (2006.01)
*G06F 19/00* (2006.01)
*G06M 11/04* (2006.01)
*C12Q 1/68* (2006.01)

(52) U.S. Cl. .............. 702/23; 700/1; 700/2; 700/7; 700/28; 700/29; 700/90; 700/266; 702/1; 702/19; 702/22; 702/27; 702/127; 422/50; 422/62; 422/68.1; 422/83; 422/98; 73/1.01; 73/1.02; 73/23.2

(58) Field of Classification Search ............ 422/50, 422/62, 68.1, 82.01, 83, 98; 436/43, 63, 436/149; 73/1.01, 1.02, 23.2; 700/1, 2, 700/7, 28, 29, 90, 266; 702/1, 19, 22, 27, 702/127

See application file for complete search history.

(56) References Cited

U.S. PATENT DOCUMENTS

| | | | |
|---|---|---|---|
| 5,571,401 A | * | 11/1996 | Lewis et al. ............. 205/787 |
| 5,820,745 A | | 10/1998 | Van Geloven |
| 5,880,352 A | | 3/1999 | Muench |
| 5,959,191 A | | 9/1999 | Lewis et al. |
| 6,077,712 A | | 6/2000 | Livingston |
| 6,331,244 B1 | | 12/2001 | Lewis et al. |
| 6,360,582 B1 | | 3/2002 | Chelvayohan et al. |
| 6,379,969 B1 | | 4/2002 | Mauze et al. |
| 6,480,730 B2 | | 11/2002 | Darrow et al. |

OTHER PUBLICATIONS

Nix, Roger, "An Introduction to Surface Chemistry," Section 3: The Langmuir Isotherm, 12 pages (Queen Mary University of London, Jan. 10, 1999) downloaded from <http://www.chem.gmc.ac.uk/surfaces/scc/>.

* cited by examiner

*Primary Examiner*—Brian Sines
(74) *Attorney, Agent, or Firm*—Goodwin Procter LLP

(57) ABSTRACT

Devices and techniques for estimating the concentration of one or more agents in a fluid environment employ a plurality of measurements of a sensor attribute that changes in response to an agent. Measurements taken before the agent/reagent combination reaches a steady-state may be used. The plurality of measurements are processed using a nonlinear, parametric model of the interaction between the sensor and the agent to determine the concentration of the agent. The model takes into account the finite capacity of a sensor reagent. The model characterizes the interaction of individual agent/reagent combinations with a set of parameters. These parameters require minimal testing to calculate. The invention enables the response of a sensor to an agent over the entire range of agent concentration levels to be efficiently and accurately characterized. The invention also enables the prediction of collective responses given parameters characterizing a plurality of agent/reagent combinations.

25 Claims, 13 Drawing Sheets

Figure 2A

METHOD AND APPARATUS FOR ANALYZING SPATIAL AND TEMPORAL PROCESSES OF INTERACTION

REFERENCE TO RELATED APPLICATIONS

This application claims the benefit of U.S. Provisional Patent Application Ser. No. 60/371,913, filed on Apr. 11, 2002, and entitled "A Method and Apparatus for Analyzing Spatial and Temporal Processes of Interaction," the entire contents of which is hereby incorporated by reference.

GOVERNMENT SUPPORT

This invention was made with government support under Contract Number N00174-97-D-0030 performed for DARPA(STO). The Government may have certain rights in the invention.

TECHNICAL FIELD

The invention generally relates to the field of chemical or biological agent detection. In particular, in one embodiment, the invention relates to a device for interpreting sensor readings to determine the concentration of an agent in a fluid environment, and the design and operation thereof.

BACKGROUND INFORMATION

A chemical sensor typically includes a vibrating membrane having a polymer coating that is capable of being loaded with vapors and interferents. As the vapor loading takes place, the mass carried by the membrane increases causing a shift in its vibration frequency. The frequency shift is a function of the type and amount of vapors loaded. In general, more than one vapor can load onto each polymer coating, but some coatings have a stronger affinity for particular vapors.

Normally, an array of sensors, each having a distinctive polymer coating, is used together; the vibration frequency of each membrane is measured and recorded. An array is usually selected to optimize a certain performance criterion of interest, such as maximizing the probability of detecting a lethal vapor of interest or minimizing the probability of false alarms. Signals representative of the vibration frequencies of an array of sensors can be interpreted to determine concentration levels of vapors present in the atmosphere.

The selection of an appropriate array has been hampered by the scanty information available on the response of coatings to vapors, and the reliability of that information. Most of the available information is based on experiments conducted on single vapor/coating pairs. These experiments are time-consuming. Additionally, processes do not exist for using the information derived from these experiments to reliably extrapolate the response of the coating to the vapor at concentration levels outside of the experimental range. Processes also do not exist for using the information derived from these experiments to reliably extrapolate the response of the coating to multiple vapors. Moreover, it is also difficult to store the information derived from these experiments efficiently. Some of the information on the reaction of coatings to vapors is based on linear models. This information may not be reliable because linear models do not adequately describe the loading process. In particular, linear models fail to account for the saturation phenomenon that relates to the finite capacity of a coating to respond to one of more vapors. As a result, the traditional processes and apparatus for estimating the concentration of a vapor in the environment do not provide an acceptable performance level.

SUMMARY OF THE INVENTION

The invention generally relates to devices and techniques for estimating the concentration of one or more agents in a fluid environment. The invention is founded on a nonlinear model of the dynamics of interaction between a sensor and a single agent. The model takes into account the finite capacity of the sensor reagent to respond to the agent. In some embodiments, the model represents the interaction as a bilinear function. In some embodiments, the model captures the stochastic aspects of the response processes. The model is parametric in that it characterizes the interaction of individual agent/reagent combinations with a set of parameters. These parameters require minimal testing to calculate. The invention addresses limitations of the prior art by enabling the response of a sensor to an agent over a wide range of agent concentration levels to be efficiently and accurately characterized. Moreover, the invention enables the prediction of collective responses given parameters characterizing a plurality of agent/reagent combinations.

Specifically, in one aspect, the invention is directed to a method of determining a concentration of an agent in a fluid environment. The method employs a plurality of measurements from a sensor of an attribute that changes in response to the agent. The method processes the plurality of measurements using a nonlinear, parametric model of the time-varying dynamics of the interaction between the sensor and the agent to determine the concentration of the agent. The model takes into account the finite capacity of a sensor reagent.

The agent, in various embodiments, is a chemical agent or a biological agent. The reagent, in some embodiments, is a polymer coating applied to the sensor. In other embodiments, the reagent is an inherent feature of the sensor. A reagent may have an affinity for an agent, for example, due to an electrical charge, a chemical attraction, a magnetic force, a mechanical force, a pressure differential, and the like.

Sensor attributes that may be used to determine the concentration of an agent in a fluid environment, in various embodiments, include (a) physical properties, such as volume or weight; (b) chemical properties, such as chemical sensitivity; (c) optical properties, such as reflectivity, emissivity or color; (d) electromagnetic properties, such as capacitance; (e) nuclear properties; or (f) other properties, such as force, stress, strain, or pressure.

In some embodiments of the invention, the model represents the time-varying dynamics of the interaction between a sensor and an agent as a bilinear function. In similar embodiments, the model represents the attribute response as a bilinear function. In some embodiments, the model embraces a plurality of reagent loading modes. The model, in some embodiments, takes into account the stochastic transport of agents, the stochastic loading of reagents, and the stochastic sensing of reagent loading.

In another aspect, the invention is directed to a system for determining a concentration of an agent in a fluid environment. The system includes a processor that processes a plurality of measurements from a sensor of an attribute that changes in response to the agent. The processor uses a nonlinear parametric model of the time-varying dynamics of interaction between the sensor and the agent to determine the concentration of the agent. The model takes into account the finite capacity of a sensor reagent.

In another aspect, the invention is directed to a method of determining a first concentration of a first agent and a second concentration of a second agent in a fluid environment. The method employs a plurality of measurements from a first and a second sensor. The measurements are of an attribute that changes in response to the first agent and the second agent. Using a nonlinear parametric model of an attribute response, the method processes the measurements to determine the first concentration and the second concentration. The model takes into account the finite capacity of reagents.

In another aspect, the invention is directed to a system for determining a first concentration of a first agent and a second concentration of a second agent in a fluid environment. The system includes a processor for processing measurements from a first sensor and a second sensor to determine the first concentration and the second concentration. The measurements are of a sensor attribute that changes in response to the first agent and a second agent. The processor uses a nonlinear, parametric model of an attribute response that takes into account the finite capacity of reagents.

According to one embodiment of the foregoing systems, the processor is an electronic component having one or more microprocessors, digital circuitry, and/or analog circuitry to analyze the plurality of measurements. In further embodiments, the processor is part of a computer system. In other embodiments, the processor is a mechanical system, a hydraulic system, a pneumatic system, a chemical system, or any other system or device capable of performing the modeling described above and below.

Some embodiments of the foregoing systems incorporate one or more sensors in signal communication with the processor. Preferably, such a sensor incorporates a reagent with a characteristic response to an agent. The reagent, in some such embodiments, is disposed on a surface of the sensor. The sensor, in some embodiments, is a vibrating membrane and the attribute is a membrane vibration frequency. Specifically, in some such embodiments, the sensor is a flexure plate wave sensor and the attribute is a vibration frequency of a plate of the flexure plate wave sensor.

In some embodiments of a system that incorporate two sensors, the first sensor incorporates a first reagent having a first characteristic response to the first agent, the second sensor incorporates a second reagent having a second characteristic response to the first agent, and the first characteristic response is dissimilar to the second characteristic response. In some such embodiments, a combination of sensor reagents are selected to optimize the speed, repeatability, and/or simplicity of determining the concentration of one or more agents. In other embodiments, a combination of sensor reagents are selected to minimize the error variance in the determining the concentration of one or more agents.

In another aspect, the invention is directed to a method of evaluating an ability of a sensor to determine a concentration of an agent in a fluid environment. According to this aspect, the sensor has an attribute that changes in response to the agent, and the method involves calculating a plurality of predicted values of the attribute using a plurality of concentrations of the agent and a nonlinear, parametric model of the time-varying dynamics of the interaction between the sensor and the agent. The model takes into account the finite capacity of a sensor reagent. The method also involves comparing the plurality of predicted values to a plurality of attribute measurements from the sensor. The plurality of predicted values and the plurality of measurements correspond to the plurality of concentrations. The ability of the sensor to determine the concentration of the agent is thereby evaluated.

In another aspect, the invention is directed to a method of characterizing a response of a reagent to an agent. In this aspect, the method involves employing a plurality of sensor measurements. Preferably, the sensor includes the reagent, and the measurements are of a sensor attribute that changes in response to the agent. The plurality of measurements corresponds to a plurality of concentrations of the agent. The method also involves calculating a plurality of parameters from the plurality of measurements and the plurality of concentrations. The plurality of parameters characterizes the response of the reagent to the agent in a nonlinear, parametric model of the time-varying dynamics of interaction between the sensor and the agent. The model takes into account the finite capacity of a sensor reagent. Constants characterizing the response of a reagent to the agent may be calculated, in some embodiments, from measurements taken while the concentration of the agent is changing.

Some embodiments of the foregoing methods further comprise determining the presence of one or more agents in the fluid environment. The presence of an agent may be determined using techniques, such as knowledge of the environment and the existence of an agent that may be released into the environment. The presence of an agent may also be determined using much more sophisticated techniques. For example, methods that involve determining the presence of one or more agents may incorporate the techniques described in U.S. patent application Ser. No. 10/385,478, filed on Mar. 11, 2003, and U.S. patent application Ser. No. 60/363,500, filed on Mar. 11, 2002, both entitled "Non-Gaussian Detection" (hereinafter "the Non-Gaussian Detection patent applications"), the entire contents of both of which are hereby incorporated by reference. Some embodiments of the foregoing systems incorporate a processor to determine the presence of one or more agents in the fluid environment. Such systems may incorporate a processor and/or detector described in the Non-Gaussian Detection patent applications. Alternatively, such systems may determine the presence of one or more agents by incorporating additional functionality into the existing processor.

Advantages and features of the invention disclosed herein will become apparent through reference to the foregoing, the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

The following drawings are not necessarily to scale, emphasis instead generally being placed upon illustrating the principles of the invention. In the following description, various embodiments of the present invention are described with reference to the following drawings, in which:

FIG. 2A is a schematic representation of interacting entities-reagent molecule B at a site on a sensor plate and molecules at sites in the air surrounding the plate site;

DETAILED DESCRIPTION OF ILLUSTRATIVE EMBODIMENTS

Embodiments of various aspects of the invention are described below. Other embodiments incorporating the concepts disclosed herein are within the spirit and scope of the invention. The described embodiments are to be considered in all respects as only illustrative and not restrictive.

Figure 1:
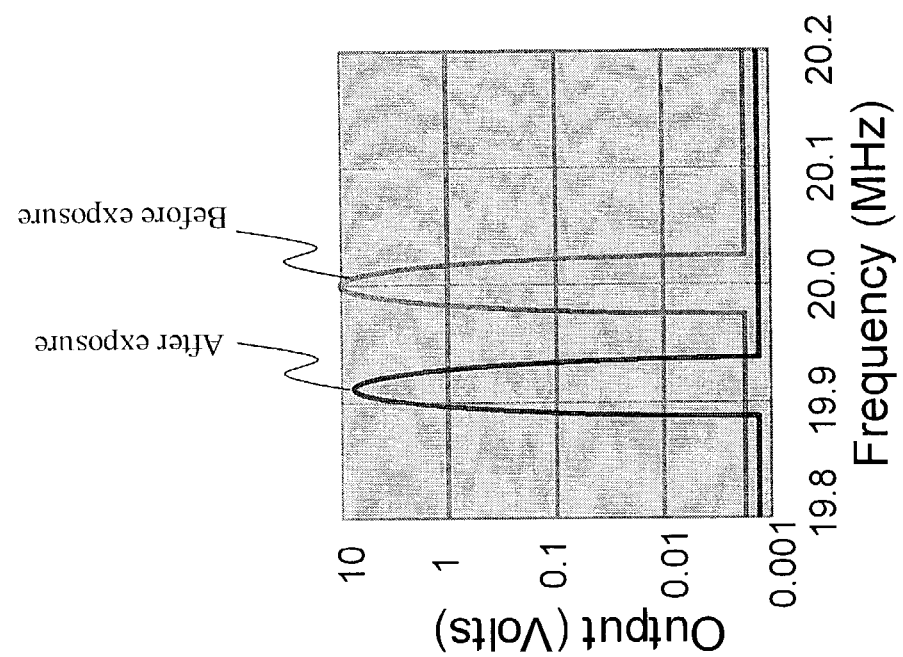
FIG. 1 is an illustration of physical components and processes that an exemplary model may describe in various embodiments of the invention.
Figure 1:
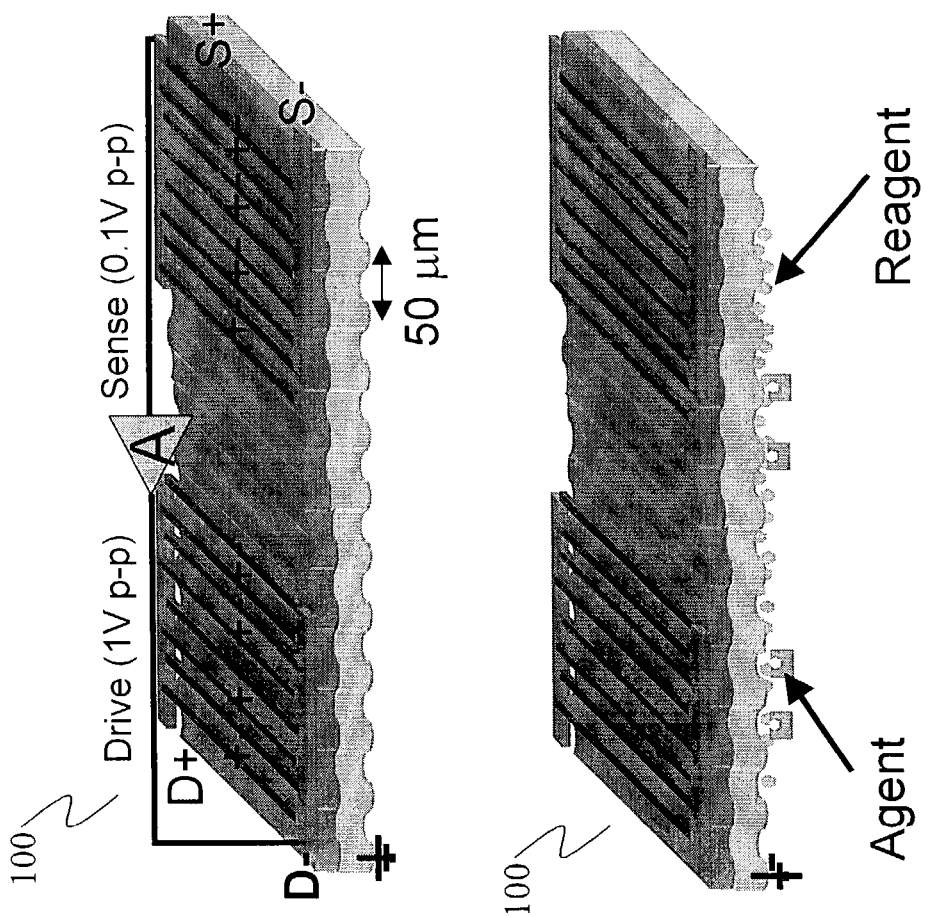

FIG. 1 depicts a sensor 100 that may be used in conjunction with, or incorporated into, the present invention. In particular, FIG. 1 depicts a flexural plate wave (FPW) sensor 100 in which the flexural plate is made of Silicon and coated with thin film piezoelectric drive and sense comb fingers on one surface. The drive comb fingers drive the plate with a sinusoidal voltage. The sense comb fingers sense the vibration frequency of the plate. An electronic circuit locks on to the resonant frequency. The opposite surface of the Silicon flexural plate is coated with a reagent. When the reagent absorbs an agent that is present in the environment, the mass of the flexural plate increases causing a shift in the vibration frequency of the plate. The concentration of an agent is estimated by interpreting the sensor readings.

Preferably, the FPW sensor 100 of FIG. 1 is placed in a gas environment and the agent is a gas vapor. Nonetheless, the FPW sensor 100 of FIG. 1 also works under the same operating principle in a liquid environment by absorbing a liquid analyte. Thus, the invention can be implemented and used in a liquid environment.

Figure 2A:
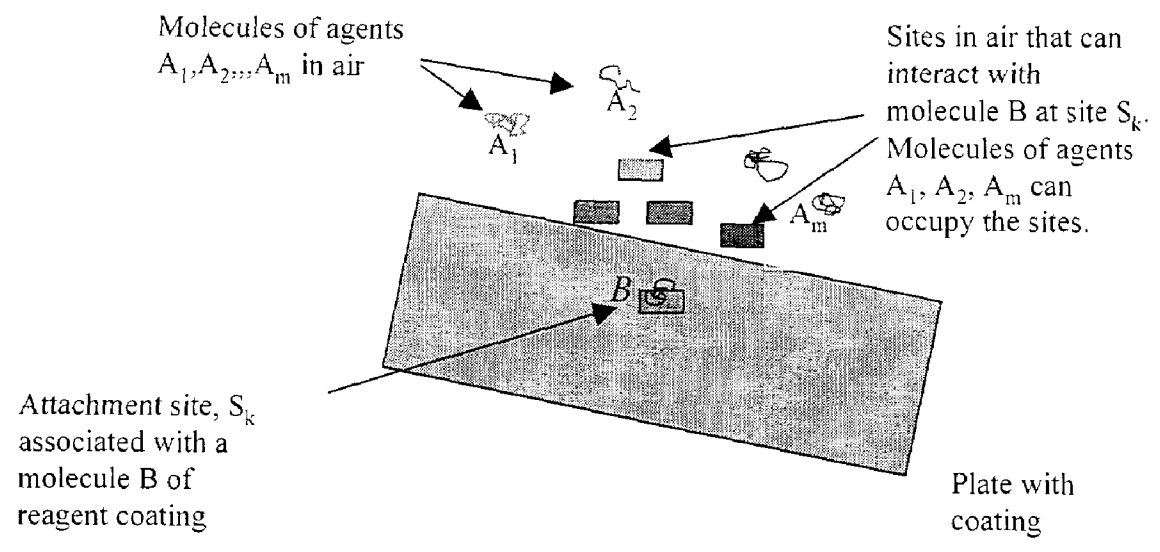
Figure 2B:
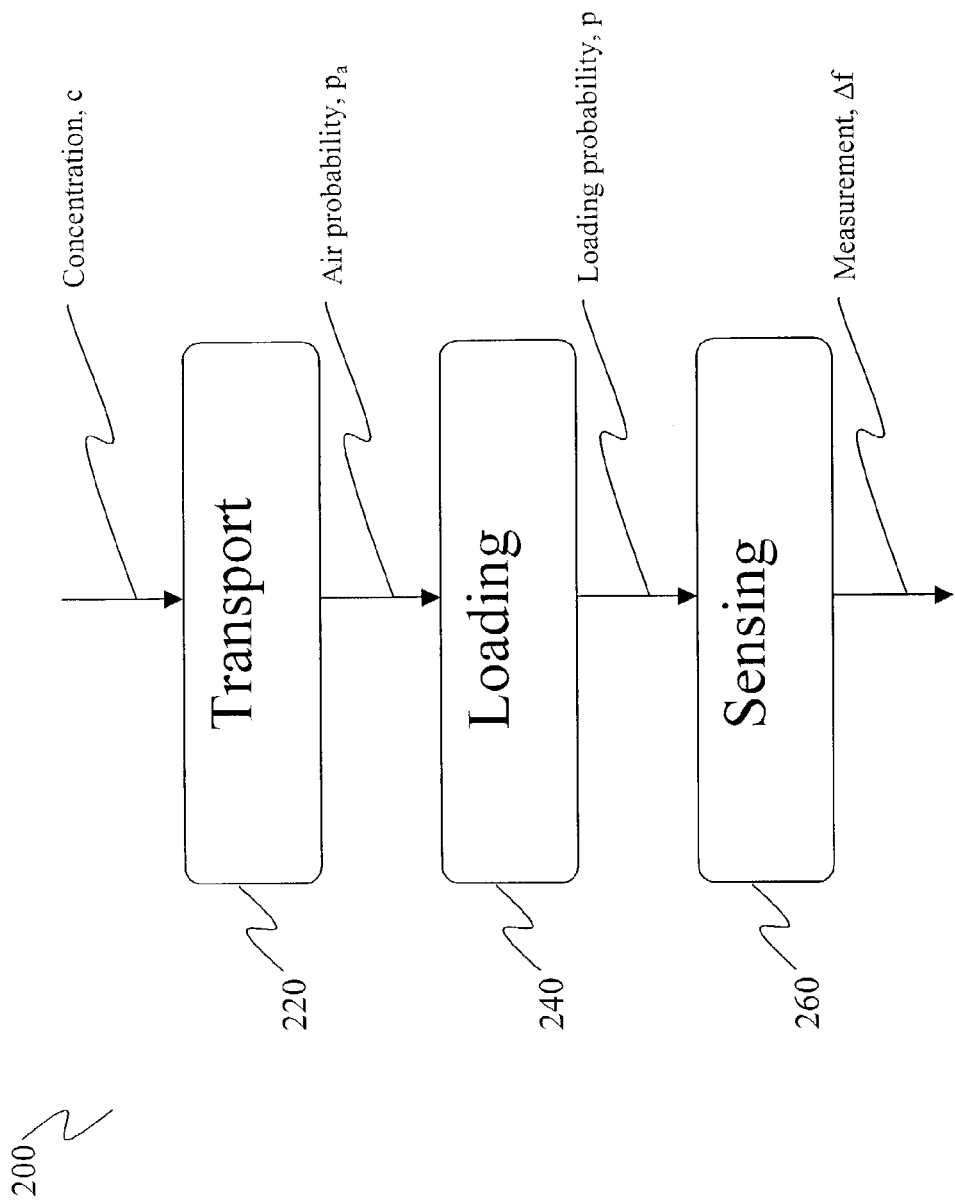
FIG. 2B is a graph depicting the interaction features of the exemplary model, which may be used in various embodiments of the invention.

FIG. 2A shows a schematic of interaction used in the development of a model of the time-varying dynamics of interaction between a sensor and an agent, in accordance with an exemplary embodiment of the invention. The sensor in the illustrative model is of the type illustrated in FIG. 1. An illustrative finite state model, in accordance with one embodiment of the invention, is developed for the different types of attachments possible for the molecule B of the coating at site $S_k$. Molecule B at site $S_k$ can interact with molecules of agents $A_1, A_2, \ldots, A_m$ that are present in the environment. FIG. 2B schematically shows the sites in air in the vicinity of site $S_k$, sites that may be empty at any instant of time or contain one of the agent molecules in the air for interaction with reagent molecule B of the coating on the sensor plate.

An illustrative model of the interaction between the sensor and a single agent is initially considered and described for simplicity. Interaction is considered in terms of sites rather than in terms of agent molecules to be able to deal with uncertainties associated with arrival or departure of molecules at the sites of interaction. While it is assumed that the plate site contains a reagent molecule of type B, it is not assumed that an agent molecule is at any air site. Air sites are the sites near the particular site $S_k$ on the plate that participate in attachment interaction with reagent molecule B at site $S_k$ on the plate. Instead, transport phenomena and the likelihood of an agent molecule occupying a particular air site at a particular instant of time is separately described.

For the illustrative model, the interaction process is assumed to be spatially independent. Alternative embodiments of the invention take spatial correlation into account at the expense of an increased number of states. For example, the interaction dependence on the location of the site on the plate is considered in alternative embodiments.

For the illustrative model, the interaction process is assumed to be dependent upon the time instant i. This feature is incorporated into the model through the time dependence of parameters and the temporal impact of other environmental characteristics such as temperature and flow rate, that modulate interaction rate. In other words, transition is dependent on the time variation of parameters of both the transport phenomenon as well as the surface chemistry of attachment and disattachment. A time interval that is small enough to enable the dynamics of interaction between the reagent molecule and agent molecules to be captured in terms of specified rules of interaction is chosen.

These rules of interaction between a reagent molecule and agent molecules may be specified from physical considerations of interaction and transport phenomena. Two types of interactions take place over the time interval. In the first type of interaction, a molecule attaches to or disattaches from the site as shown. This interaction is described symbolically by the following:

(a)

In the second type of interaction, there is no change in status of attachment or disattachment.

This interaction is described symbolically by the following:

$$B \underset{kb}{\longleftrightarrow} B \qquad (b)$$

$$AB \underset{kab}{\longleftrightarrow} AB$$

Equations (a) and (b) are a complete prescription of rules of interaction that can take place over a given time interval. Thus, for example in (a), B and A may combine with likelihood or rate parameter $k_f$ to lead to the attachment outcome AB or an attachment at site $S_k$ of type AB may disassociate leading to separation of A and B at rate or likelihood kb. For the type of processes shown by (b), directions of arrows do not have any relevance with no change in status. The rate parameters of (a) and (b) are related.

The type of interactions at site B, which take into account the fact that molecules that lead to interaction come from one of the sites in air, is the loading feature of the model. The phenomenon that deals with transport aspects of the movement of molecules to and from the individual sites in the air is the transport feature of the illustrative model.

Since the outcome of interactions at a particular site or whole plate is sensed from the value of an attribute associated with the outcomes, the expected uncertainty in sensing an outcome is of interest. This uncertainty is the uncertainty of the interaction process and not the uncertainty associated with the sensing process itself (i.e., errors of sensing). Since sensing is done on a macroscopic spatial scale, for example, through the change in frequency of the vibrating plate due to addition or disassociation of mass, we can evaluate the combined average impact of all the sites.

The goal of the model development process is to determine an appropriate way to represent the relationship between an agent concentration and an attribute measurement. FIG. 2B depicts features of the time-varying dynamics of interaction between a sensor and an agent that are represented in the illustrative model of an embodiment of the invention. The three features of the response process shown in FIG. 2B are described in the illustrative model: specifically, molecular transport of the agent 220, mass loading of the reagent 240, and the load sensing 260.

The dynamic portion of the model of the response of a reagent to a single agent, of the illustrative embodiment, is represented by a set of three equations, each describing a feature of the model. The illustrative embodiment represents the response dynamics as a first order causal model.

The illustrative model accounts for diffusion of an agent from the environment to the air-reagent interface. The probability of an agent molecule being at a site in the environment that will enable it to interact with the reagent is a function of the concentration of the agent. The molecular transport feature of the illustrative dynamic model 220 is described by the equation:

$$p_a = \frac{k_t c}{1 + k_t c} \qquad (1)$$

where $p_a$ is the probability that the agent molecule will be at a site in the environment that will enable it to interact with the plate coating; $k_t$ is a constant describing the probability of an agent molecule being at a given site in the air; and c is the concentration of the agent in the environment. The constant $k_t$ is dependent on the molecular mass properties of the agent, as well as transport characteristics. Equation (1) represents a dynamic state because the concentration of the agent (c) may be changing with time in the illustrative model. The illustrative dynamic model describes molecular transport in an environment in which there is a continuous flow. In alternative embodiment, a different equation can be used to describe molecular transport in an environment in which there is a finite volume exposure.

Loading at a given location on the reagent depends upon the site type and the reaction type. In a model of a sensor of the type illustrated in FIG. 1, the position and state of the plate and the coating may affect the site type. The mass loading of the reagent feature of the illustrative dynamic model 240 is described by the equation:

$$\frac{\partial p}{\partial t} = -c_s(1 - p_a)p + c_\infty(1 - p)p_a \qquad (2)$$

where p is the probability of the agent being loaded on the plate; $c_s$ is the coefficient of desorption of the reagent, and $c_\infty$ is the coefficient of absorption of the reagent. The term $(1-p_a)$ in equation (2) represents the vacancy level of the environment and the term (1-p) in equation (2) represents the vacancy level of the reagent coating. The rate of mass loading is the difference between the rate of absorption and the rate of desorption. In the illustrative model, the coefficients $c_s$ and $c_\infty$ are parameters describing single rates in the agent/reagent combination.

Individual loading and unloading rates are modulated by the presence of the agent, the combined presence of other agents, the type of linking site, and transport and environmental effects. Accordingly, in the illustrative model, the coefficients $c_\infty$ and $c_s$ may also describe an aggregate of a plurality of loading and unloading rates, respectively, in the agent/reagent combination. In an alternative embodiment, the model is extended to incorporate additional dynamic parameters to characterize additional loading or unloading rates, in the agent/reagent combination. For example, the coefficient $c_{\infty 1}$ may be incorporated into the model to represent a first loading mode while the coefficient $c_{\infty 2}$ may be incorporated into the model to represent a second loading mode.

The load sensing feature of the illustrative dynamic model 260 is described by the equation:

$$\Delta f = k_m p \qquad (3)$$

where $\Delta f$ if the change in vibration frequency; and $k_m$ is a constant characterizing the impact of mass loading on the change in frequency. Equation (3) represents a dynamic state because the probability of the agent being loaded on the plate (p) may be changing with time in the illustrative model. Loading sensing is described with respect to larger spatial scale than the other aspects of the model, as a collective response. Although the illustrative model uses the change in the vibration frequency $\Delta f$ as the sensor attribute to be modeled and measured to determine agent concentration, other sensor attributes are used in alternative embodiments.

The steady-state portion of the model of the response of a reagent to a single agent, of the illustrative embodiment, is represented by a set of three equations, each again describing features of the model. The equations are easily derived from the first order dynamic model by considering the special case of steady-state conditions. In steady-state conditions, equations (1) and (3) remain the same.

Since in a steady-state condition the probability of the agent being loaded on the plate (p) does not change with time, equation (2) can be simplified. The mass loading of the reagent feature of the illustrative steady-state model is described by the equation:

$$p = \frac{k_l\left(\frac{p_a}{1-p_a}\right)}{1+k_l\left(\frac{p_a}{1-p_a}\right)} \quad (4)$$

where $k_l$ is defined as the coefficient of absorption of the reagent $c_\infty$ divided by the coefficient of desorption of the reagent $c_s$. The steady-state portion of the model of the illustrative embodiment corresponds to the Langmuir Isotherm.

Finally, combining the dynamic equations and the steady-state equations results in a comprehensive illustrative model, in accordance with one embodiment of the invention. The comprehensive illustrative model of the time-varying interaction between a sensor comprising a single reagent and a single agent is described by the equation:

$$\Delta f = \frac{k_T c}{1+k_{lt} c} \quad (5)$$

where $k_T$ is defined as the product of $k_m$, $k_l$, and $k_r$; and $k_{lt}$ is defined as the product of $k_l$ and $k_r$. The illustrative model is bilinear. At low loading, the change in frequency may be approximated by the equation:

$$\Delta f = k_T c \quad (6)$$

Figure 3:
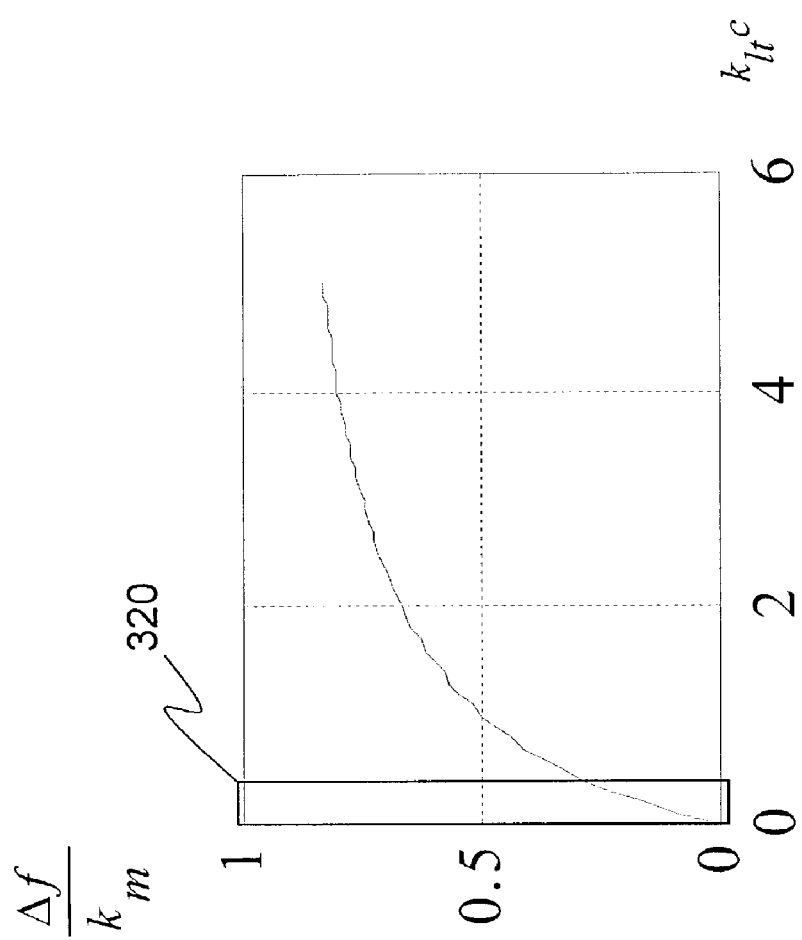
FIG. 3 is a graph depicting the nonlinear response of a sensor attribute to a range of agent concentrations in accordance with an illustrative embodiment of the invention.

In accordance with the illustrative model described in association with FIG. 2, FIG. 3 depicts an attribute response as a nonlinear function of agent concentration in the environment. The nonlinearity is a feature of the agent/reagent interaction properties, and not a feature of reagent coating size. As FIG. 3 illustrates within region 320, the response of the reagent to very low concentrations of the agent is very close to linear. However, as shown outside region 320, the finite capacity of the reagent to respond to the agent becomes apparent at higher concentrations of the agent where the response of the reagent becomes less pronounced. Linear models fail to adequately describe the response of the reagent when saturation becomes a factor.

In particular, FIG. 3 depicts the change in vibration frequency divided by one parameter, on the vertical axis, as a bilinear function of agent concentration multiplied by another parameter, on the horizontal axis. Although the invention is not limited to a bilinear model, it may be preferable to use a bilinear model when practicing the invention for a number of reasons. A bilinear model is the simplest upgrade to a linear model to describe the observed nonlinearity of transient and steady-state responses. A bilinear model requires only one more parameter to substantially improve upon a linear model. Additionally, a bilinear model approximates even higher order models, such as trilinear models. A bilinear model permits linear models to be extended through measurement-based pseudo-linearization. A bilinear model may permit the use of Markov processes methods to be used for detection based on transient measurements. Unlike linear modeling, bilinear modeling permits the separate estimation of parameters of sensing, transport, and loading. Additionally, the model structure permits scalability and the use of smaller size and more sensitive coatings.

Figure 4:
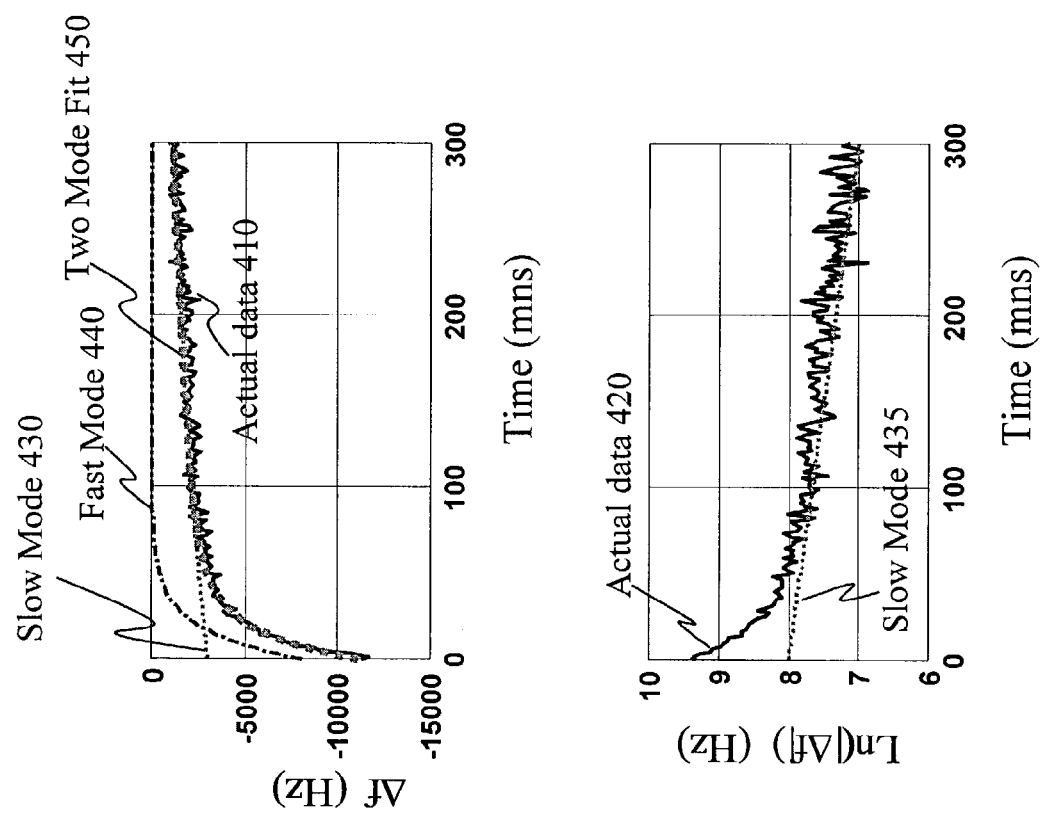
FIG. 4 is a graph depicting the transient response, where one and two reagent loading modes exist, of a sensor attribute after exposure to a finite sample of an agent, in accordance with an illustrative embodiment of the invention.

Referring to FIG. 4, the results of an experiment are depicted. In particular, FIG. 4 depicts the transient response of a reagent after exposure to, and removal of, a finite sample of an agent. While the reagent is exposed to the agent, it absorbs the agent. Once the agent is removed from the environment, the reagent begins to desorb the agent and the desorption process follows the pattern depicted in FIG. 4. In particular, FIG. 4 illustrates the change in sensor vibration frequency on the vertical axis of the top graph and the natural log of the change in sensor vibration frequency on the vertical axis of the bottom graph, both with respect to time on the horizontal axis. On both the top and bottom graphs, the measured change in vibration frequency is labeled as Actual Data 410 or 420.

There may be more than one mode of desorption as illustrated in FIG. 4. FIG. 4 specifically shows how Actual Data may represent the summation of a Slow Mode of desorption 430 and a Fast Mode of desorption 440. FIG. 4 also shows how closely the model can approximate the Actual Data 410 with a Two Mode Fit 450. Similarly, there may be more than one mode of absorption.

The measurements of a transient response, such as illustrated in FIG. 4, may be employed to calculate parameters characterizing the response of a reagent to an agent in one aspect of the invention. Unlike the Langmuir Isotherm, the model of the present invention represents the dynamics of interaction between a sensor and an agent. The invention does not require the reagent/agent combination to have reached a steady-state condition before measurements can be taken to characterize the response of a reagent to the agent.

Figure 5:
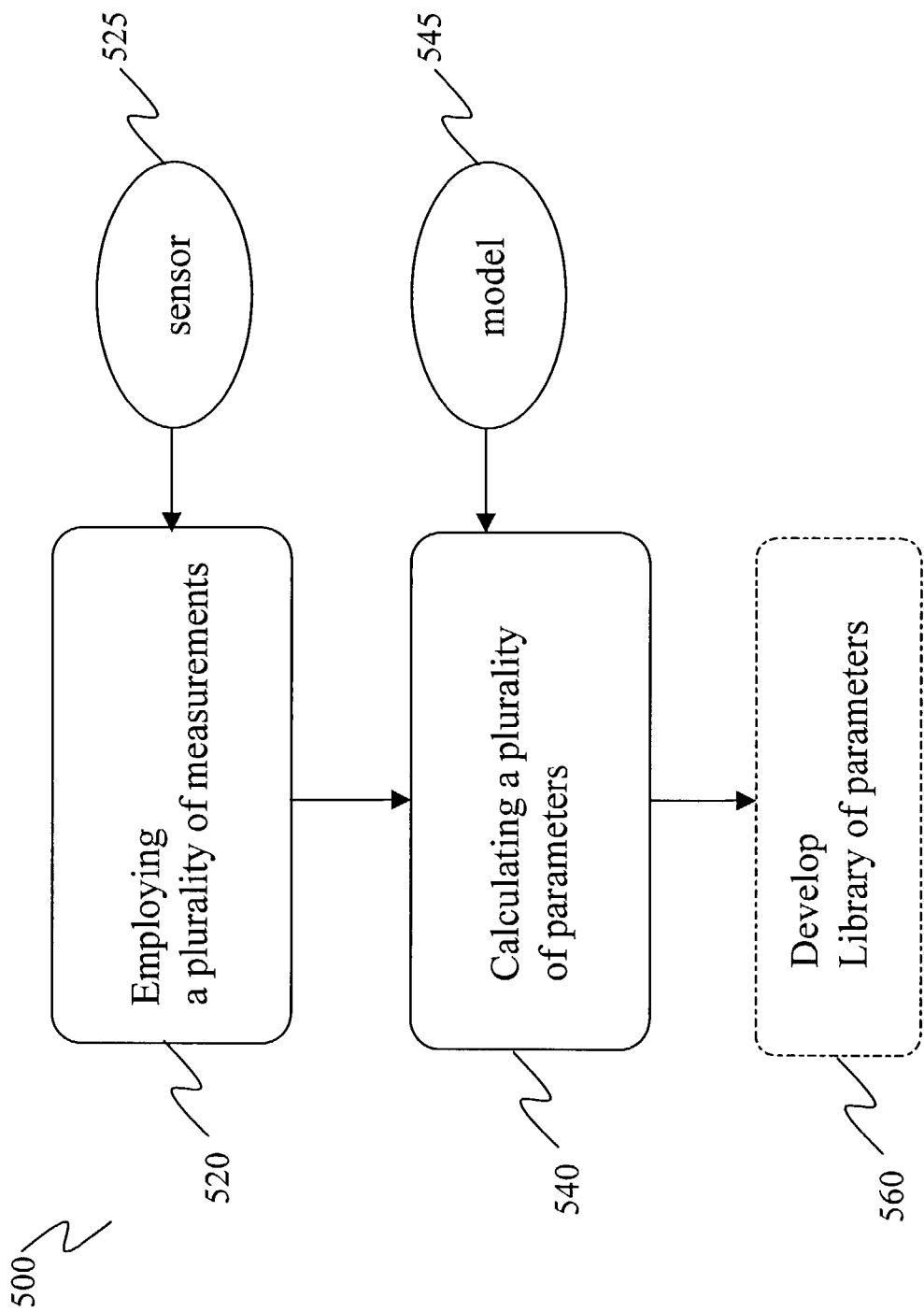
FIG. 5 is a flow diagram depicting a method of characterizing a response of a reagent to an agent in accordance with an illustrative embodiment of the invention.

Referring now to FIG. 5, a method 500 of characterizing a response of a reagent to an agent is described. In step 520 of the method 500 of FIG. 5, a plurality of measurements of an attribute of a sensor 525 that changes in response to the agent are employed. In some embodiments, the sensor 525 whose attribute is being measured comprises a reagent. In the illustrative embodiment, the reagent comprises a coating on a flexural plate. Each measurement will correspond to an agent concentration. Measurements taken while the concentration of the agent is changing over time can be used to characterize the response of a reagent to the agent.

In step 540 of the method 500 of FIG. 5, a plurality of parameters are calculated from the plurality of measurements and the corresponding concentrations. The parameters are calculated using a model 545 of the time-varying dynamics of interaction between the sensor and the agent. The model 545 takes the finite capacity of the reagent into account. In one embodiment of the method 500 of FIG. 5, equation (5) is used to calculate the parameters. The parameters characterize an individual agent/reagent combination.

As illustrated in optional step 560 of the method 500 of FIG. 5, a library of parameters representing a number of individual agent/reagent combinations may be developed. Such a library may be useful in selecting an array of sensors that is suited to a particular environment or optimized for a specific criteria.

Figure 6:
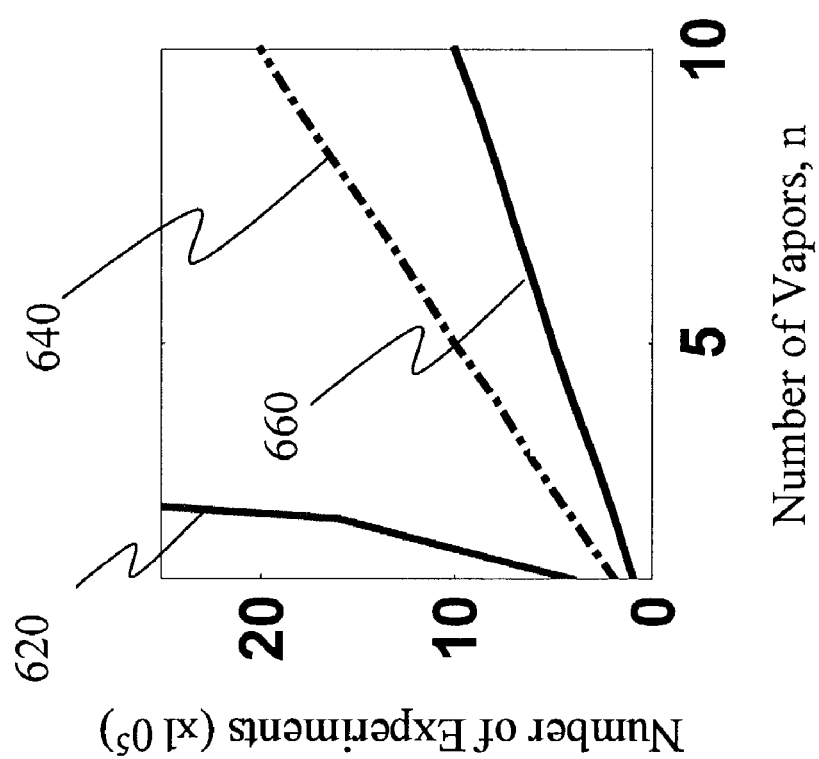
FIG. 6 is a graph comparing the experimentation required to predict reagent response based on a neural net approach, based on a steady-state approach, and based on an illustrative embodiment of the invention.

Referring now to FIG. 6, an advantage of the present invention is illustrated. The amount of time required to characterize a number of agents using various approaches is compared. The vertical axis in the FIG. 6 represents the number of experiments required while the horizontal axis represents the number of agent vapors, designated n with respect to FIG. 6 only. It is assumed that an experiment for each approach will take 30 minutes. Curve 620 represents the number of experiments required using the neural network approach. Specifically, curve 660 describes the function $c^n$ where c is the number of grid points needed per vapor and n is the number of agents. For comparison purposes, it assumed that four grid points per vapor will suffice using the neural network approach. Curve 640 represents the number of experiments required using the steady-state approach. Specifically, curve 640 describes the function 2n where n is the number of agents. Curve 660 represents the number of experiments required using the approach described with respect to the present invention. Specifically, curve 660 describes the function n where n is the number of agents.

As FIG. 6 illustrates with curve 620, non-parametric models (i.e., neural networks) require too many experiments to be viable when more than a small number of agents are of interest. Parametric models, as FIG. 6 illustrates with curve 640 and curve 660, require a much more reasonable number of experiments when more than a small number of agents are of interest. Using a parametric model, the required number of experiments is a linear function of the number of agents to be characterized. Nonetheless, the present invention is an improvement over the steady-state approach because it requires half as many experiments to be performed to characterize any number of agents. This is possible because more information can be derived from any single experiment for the present invention. Unlike the steady-state approach, the present invention can characterize an agent based on measurements taken while the concentration of the agent is changing. Accordingly, a single experiment represents more information that can be employed by the present invention than information that can be employed by the steady-state approach.

Figure 7:
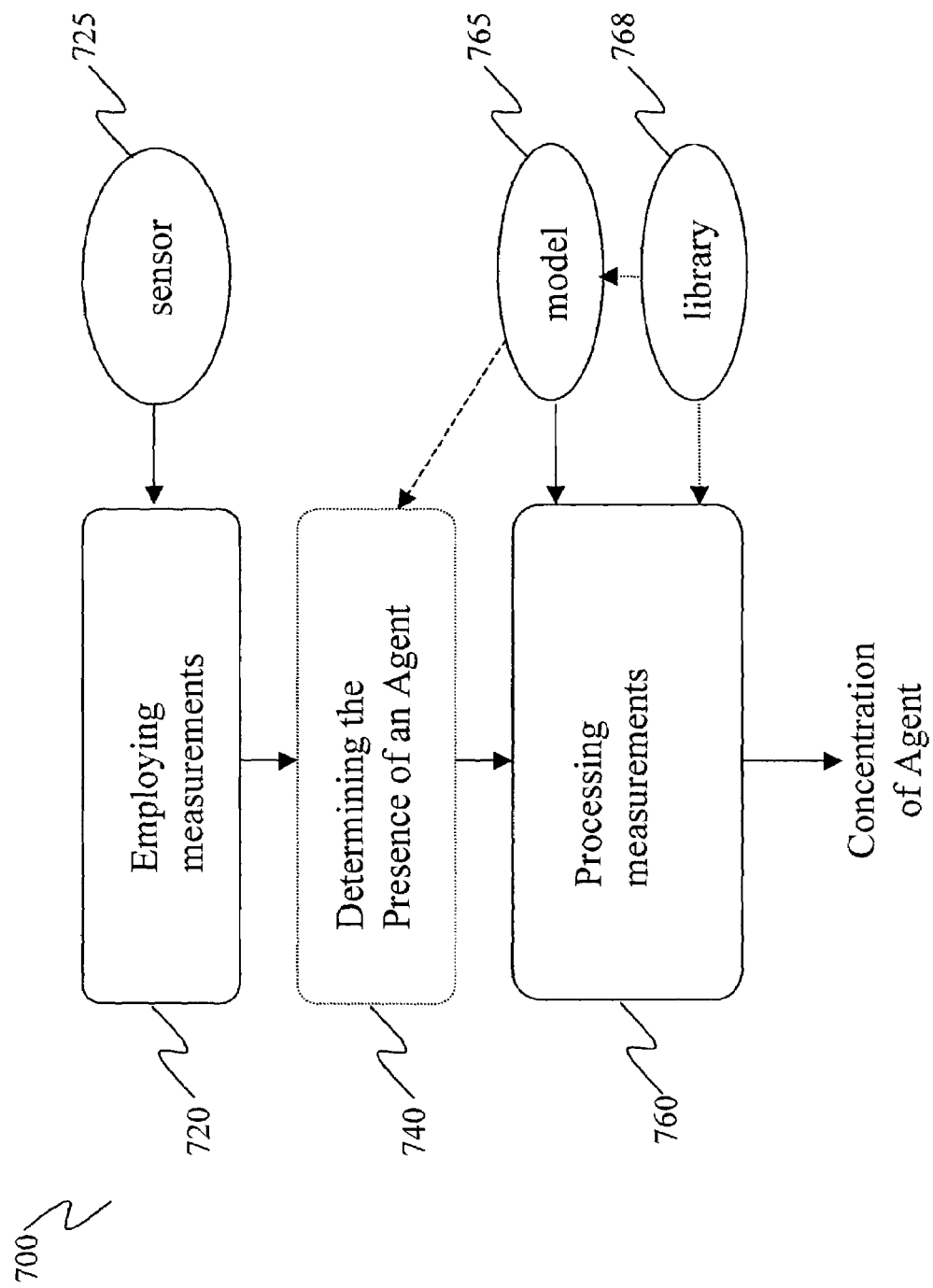
FIG. 7 is a flow diagram depicting a method of determining the concentration of an agent in a fluid environment, in accordance with an illustrative embodiment of the invention.

Referring now to FIG. 7, a method 700 of determining the concentration an agent in a fluid environment is described. In step 720 of the method of FIG. 7, a plurality of measurements of an attribute of a sensor 725 that changes in response to the agent are employed. In some embodiments, the sensor 725 whose attribute is being measured comprises a reagent. In the illustrative embodiment, the reagent is formed as a coating on a flexural plate. The measurements may be taken before the agent/reagent combination reaches a steady-state condition. The measurements may take the form of sensor readings.

In step 760 of the method of FIG. 7, the concentration of the agent is determined by processing the plurality of measurements using a nonlinear, parametric model of the time-varying dynamics of interaction between the sensor and the agent 765. The model 765 takes the finite capacity of the reagent into account. In one embodiment of the method 700 of FIG. 7, equation (5) is used to determine the concentration of the agent. The parameters characterizing the individual agent/reagent combination are incorporated into the model 765 in one embodiment. In an alternative embodiment, the model 765 uses parameters characterizing the individual agent/reagent combination from a database 768. The sensor readings are thereby interpreted. In one embodiment, the sensor readings are interpreted in real-time. In an alternative embodiment, the sensor readings are interpreted after being recorded.

Some embodiments of the method illustrated by FIG. 7 include an additional step, step 740. In step 740, the presence of the first agent is determined. Such embodiments use the techniques described in the Non-Gaussian Detection patent applications. In the Non-Gaussian Detection techniques, the signal of interest corresponds to sensor attribute measurements associated with the response signature of the first agent. The one or more second signals correspond to sensor attribute measurements associated with one or more interferent. In some such embodiments, the determining step uses the same model 765 of the attribute response used in step 760. In such embodiments, parameters characterizing the relevant agent/reagent combination are also used. These parameters are incorporated into the model 765 in one embodiment and accessed from a database 768 in an alternative embodiment. The sensor readings are thereby interpreted.

A system to implement the method of FIG. 7 in some embodiments, includes a processor. The processor, in an illustrative embodiment of such a system, determines the concentration of the agent by processing the plurality of measurements using the same model described with respect to FIG. 7. The processor, in various illustrative embodiments, is an electronic component having one or more microprocessors, digital circuitry, and/or analog circuitry to analyze the plurality of measurements. In further illustrative embodiments, the processor is part of a computer system. In other illustrative embodiments, the processor is a mechanical system, a hydraulic system, a pneumatic system, a chemical system, or any other system or device capable of performing the modeling described with respect to FIG. 7.

In some illustrative embodiments, a system to implement the method of FIG. 7 may further include one or more sensors in signal communication with the processor. A sensor, in such an embodiment, includes a reagent and has an attribute that changes in response to the agent. In the illustrative embodiment, the reagent is a coating disposed on the flexural plate of the FPW sensor and the attribute is the vibration frequency. The attribute measurements are communicated to the processor as sensor readings.

In some illustrative embodiments of a system to implement the method 700 of FIG. 7, the processor incorporates additional functionality into the existing processor to implement Step 740 of FIG. 7. Alternative illustrative embodiments of a system to implement the method of FIG. 7 further include a detector and/or second processor, such as described in the Non-Gaussian Detection patent applications, to implement Step 740 of FIG. 7. In these embodiments the detector and/or the second processor is in signal communication with the first processor. The detector and/or second processor determines the presence of one or more agents in the fluid environment.

Figure 8:
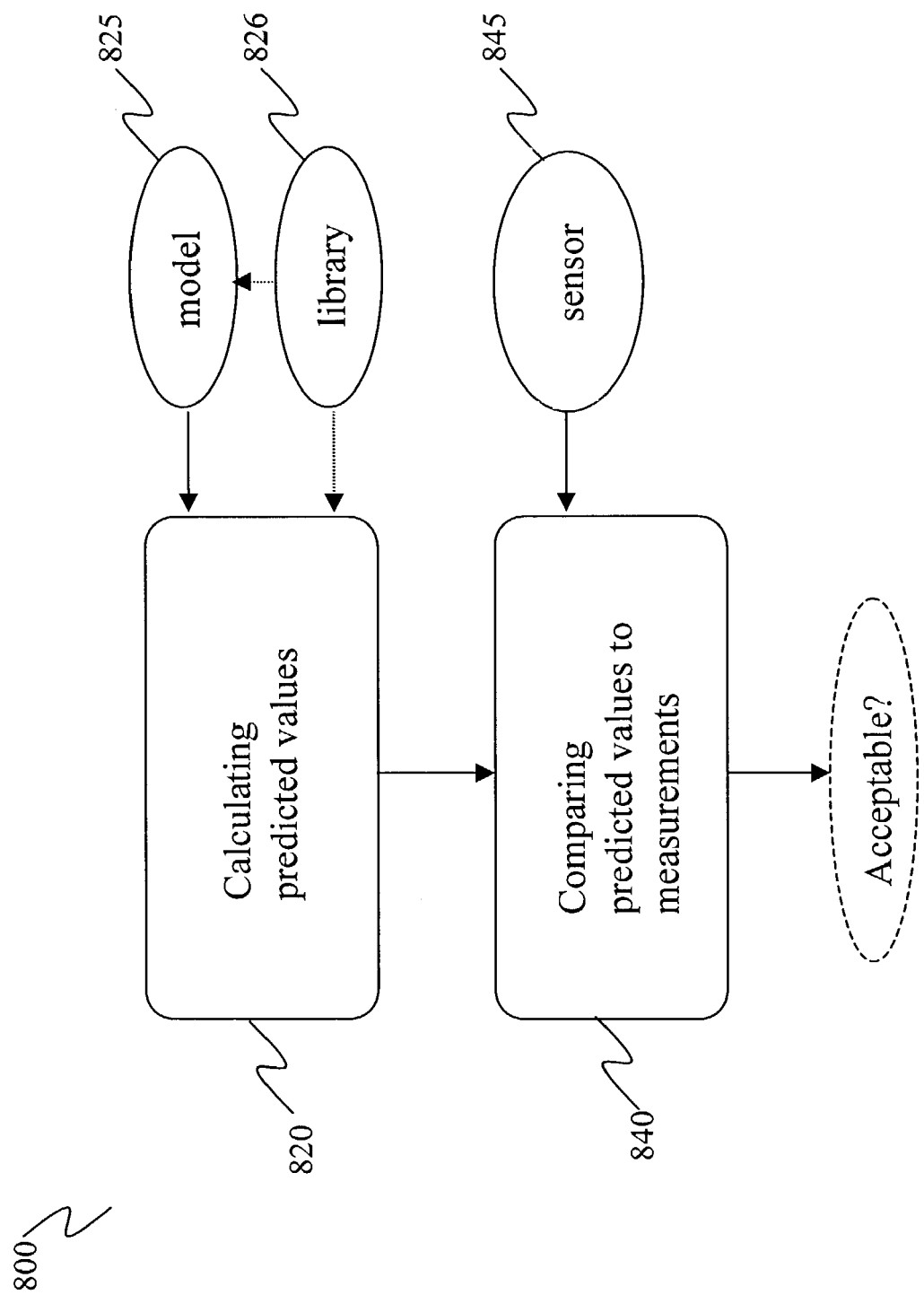
FIG. 8 is a flow diagram depicting a method of evaluating the ability of a sensor to determine the concentration of an agent in a fluid environment, in accordance with an illustrative embodiment of the invention.

Referring now to FIG. 8, a method 800 of evaluating an ability of a sensor 845 to determine a concentration of an agent in a fluid environment is described. The sensor 845 being evaluated has an attribute that changes in response to the agent. The sensor 845, in some illustrative embodiments, comprises a reagent. In the illustrative embodiment, the reagent is formed as a coating on a flexural plate. In step 820 of the method 800 of FIG. 8, a plurality of predicted values of the attribute are calculated using a plurality of concentration of the agent and a non-linear, parametric model of time-varying dynamics of interaction between the sensor and the agent 825. The model 825 takes into account the finite capacity of a sensor reagent to respond to an agent. In one illustrative embodiment of the method 800 of FIG. 8, equation (5) is used to calculate the plurality of predicted values of the attribute. Parameters characterizing the individual agent/reagent combination are incorporated into the model 825 in one embodiment. In an alternative illustrative embodiment, the model 825 uses parameters characterizing the individual agent/reagent combination from a database 826.

In step 840, the method 800 compares the plurality of predicted values to a plurality measurements of the attribute to evaluate the ability of the sensor 845 to determine the concentration of the agent. For each concentration, there is a corresponding predicted value and measurement. The measurements may be taken before the agent/reagent combination reaches a steady-state condition. The measurements may take the form of sensor readings.

The illustrative model can be generalized to the situation in which a sensor including a single reagent has the opportunity to interact with more than one agent in the environment. The molecular transport feature of the more general illustrative dynamic model is described by the equation:

$$p_{a_i} = \frac{k_{li}c_i}{1+\sum_i k_{ti}c_i} \quad (7)$$

where $p_{ai}$ is the probability that the $i^{th}$ agent molecule will be at a site in the environment that will enable it to interact with the plate coating; $k^{ti}$ is a constant describing the probability of the $i^{th}$ agent molecule being at a given site in the air; and $c_i$ is the concentration of the $i^{th}$ agent in the environment.

The mass loading of the reagent feature of the more general illustrative dynamic model is described by the equation:

$$\frac{\partial p_i}{\partial t} = -c_{s_i}\left(1-\sum_j p_{a_j}\right)p_i + c_{\infty_i}\left(1-\sum_j p_j\right)p_{a_i} \quad (8)$$

where $p_i$ is the probability of the $i^{th}$ agent being loaded on the plate at a given site; $c_{si}$ is the coefficient of desorption of the reagent with respect to the $i^{th}$ agent, and $c_{\infty i}$ is the coefficient of absorption of the reagent with respect to the $i^{th}$ agent. Both i and j range from 1 to n, where n is the number of agents. Each probability must between 0 and 1 inclusive. Moreover, as the equation indicates, there is a vector of probabilities for each of the agents at a given site.

The load sensing feature of the more general illustrative dynamic model is described by the equation:

$$\Delta f = \sum_j k_{mj} p_j \quad (9)$$

where $\Delta f$ if the change in vibration frequency; and $k^{mj}$ is a constant characterizing the mass loading.

The steady-state portion of the model of the response of a reagent to a plurality of agents, of the illustrative embodiment, is represented by a set of three equations, each again describing features of the model. The equations can be derived from the more generalized dynamic model by considering the special case of steady-state conditions. In steady-state conditions, equations (7) and (9) remain the same.

Since in a steady-state condition the probability of any particular agent being loaded on the plate, $p_i$, does not change with time, equation (8) can be simplified. The mass loading of the reagent feature of the more general illustrative steady-state model is described by the equation:

$$p_i = \frac{k_{ti}k_{li}c_i}{1+\sum_j k_{tj}k_{li}c_j} \quad (10)$$

where $k_{li}$ is defined as the coefficient of absorption of the $i^{th}$ agent by the reagent ($c_{\infty i}$) divided by the coefficient of desorption of the $i^{th}$ agent by the reagent ($c_{si}$).

Finally, combining the generalized, dynamic equations and the generalized, steady-state equations results in a more comprehensive illustrative model, in accordance with one embodiment of the invention. The comprehensive illustrative model of the time-varying interaction between a sensor comprising a single reagent and a plurality of agents is described by the equation:

$$\Delta f = \frac{\sum_j k_{Tj}c_j}{1+\sum_j k_{1tj}c_j} \quad (11)$$

where $k_{Tj}$ is defined as the product of $k_{mj}$, $k_{ij}$, and $k_{tj}$; and $k_{ltj}$ is defined as the product of $k^{ij}$ and $k_{tj}$. The illustrative model is bilinear. At low loading, the change in frequency may be approximated by the equation:

$$\Delta f = \sum_j k_{Tj}c_j \quad (12)$$

Figure 9:
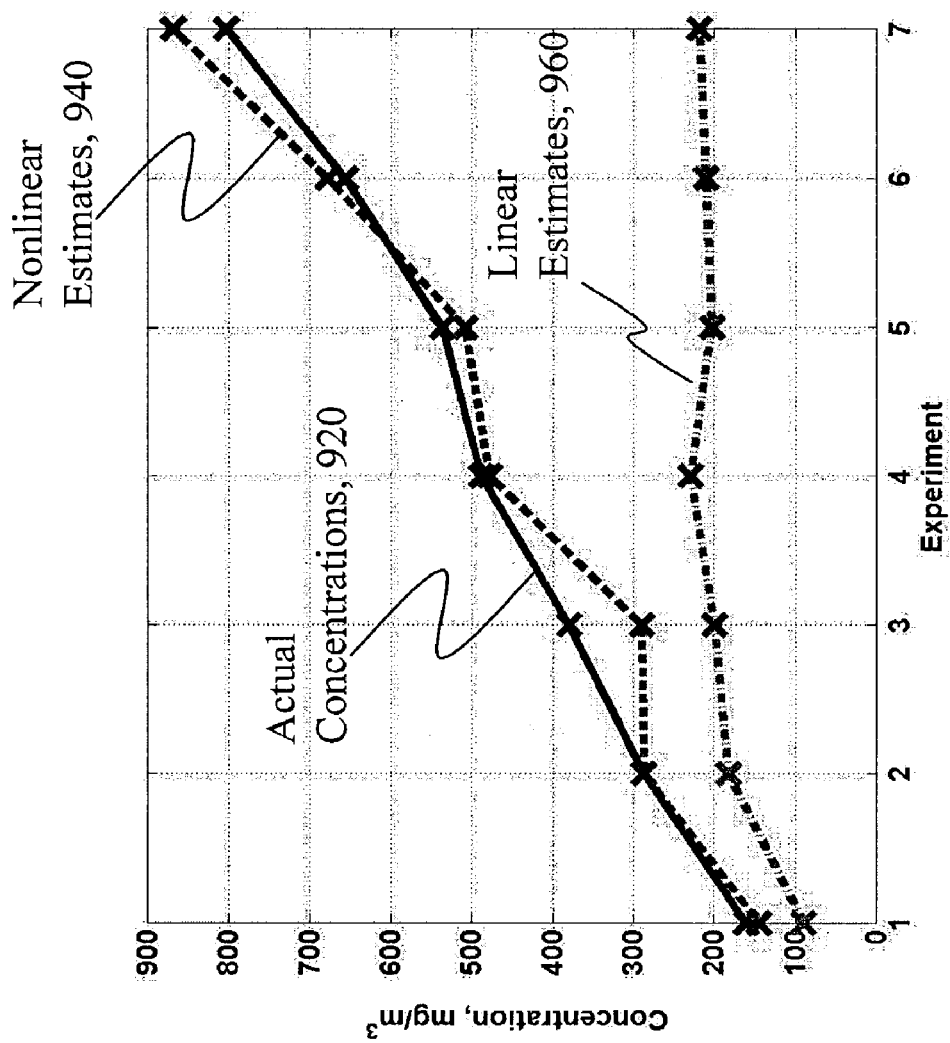
FIG. 9 is a first graph comparing the actual concentration of an agent to the concentration predicted by interpreting sensor readings using a prior art linear model and the concentration predicted by interpreting sensor readings using a model in accordance with an illustrative embodiment of the invention.
Figure 10:
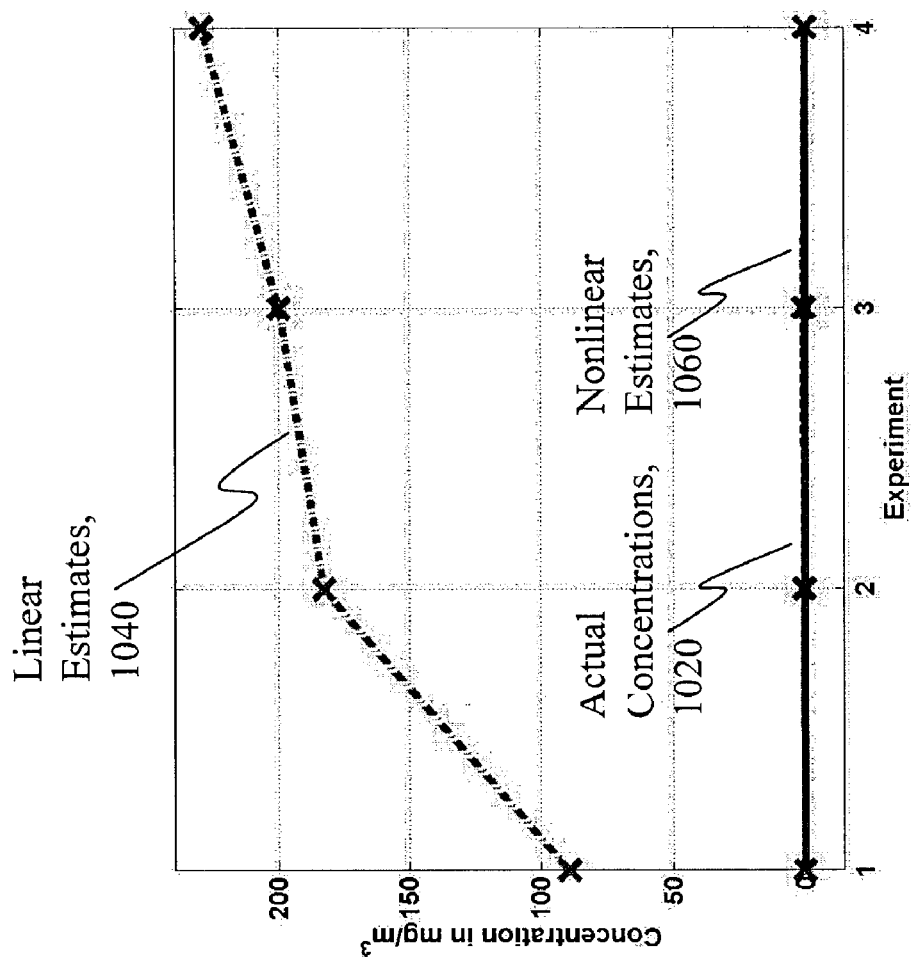
FIG. 10 is a second graph comparing the actual concentration of an agent to the concentration predicted by interpreting sensor readings using a prior art linear model and the concentration predicted by interpreting sensor readings using a model in accordance with an illustrative embodiment of the invention.

FIGS. 9 and 10 illustrate an advantage of the generalized illustrative model of one embodiment of the invention with respect to prior art linear models. The prior art linear models do not provide an acceptable performance level where the sensor may interact with more than one agent.

FIG. 9 is a graph comparing the actual concentration of an agent to the concentrations predicted by interpreting sensor readings at those concentrations using a prior art linear model and using a generalized model in accordance with an illustrative embodiment of the invention. The actual concentration of DMMP is shown by curve 920. Curve 940 represents the concentration of DMMP estimated from sensor readings using a linear model. Curve 960 represents the concentration of DMMP estimated from sensor readings using the present invention. Both estimations were based on an environment in which Toluene could potentially be present, but was not in fact present. As FIG. 9 illustrates, use of the prior art linear model results in an underestimation of the concentration of DMMP. Accordingly, use of the prior art linear model may result in missed detection of an agent. In contrast, use of a model in accordance with the invention results in a more accurate estimation.

FIG. 10 is a graph comparing the actual concentration of an agent to the concentrations predicted by interpreting sensor readings at those concentrations using a prior art linear model and using a model in accordance with an illustrative embodiment of the invention. The actual concentration of DMMP is shown by curve 1020. Curve 1040 represents the concentration of DMMP estimated from sensor readings using a linear model. Curve 1060 represents the concentration of DMMP estimated from sensor readings using the present invention. Both estimations were based on an environment in which Toluene could potentially be present. In fact, Toluene was present but DMMP was not present. As FIG. 10 illustrates, use of the prior art linear model results in an overestimation of the concentration of DMMP. Accordingly, use of the prior art linear model may result in a false alarm. In contrast, use of a model in accordance with the invention results in a more accurate estimation.

An array of sensors can be used, in conjunction with or as a component of the illustrative embodiments of the invention, to determine the concentration of more than one agent in the environment. Each sensor in the array should have a distinct reagent. The value of the measured attribute of each sensor accordingly provides distinct information regarding the environment.

In illustrative embodiments of the invention used to determine the concentration of more than one agent in the environment, a response matrix based on the model of interaction may be used to relate a vector of sensor attribute values to a vector of agent concentrations. This approach is described for a two sensor array by the equation:

$$\begin{bmatrix} \Delta f_1 \\ \Delta f_2 \end{bmatrix} = H(\Delta f_1, \Delta f_2) \begin{bmatrix} c_{A_1} \\ c_{A_2} \end{bmatrix} \quad (13)$$

where $\Delta f_1$ is the vibration frequency of the first sensor; $\Delta f_2$ is the vibration frequency of the second sensor; H is the response matrix; $c_{A_1}$ is the concentration of the first agent; and $c_{A_2}$ is the concentration of the second agent. While equation (13) features vibration frequency as the sensor attribute, alternative embodiments similarly use other sensor attributes. Equation (13) can easily be extended for arrays with more than two sensors.

The response matrix H, in some embodiments, takes advantage of the bilinear nature of the model of interaction and incorporates the parameters characterizing the reaction of a single sensor reagent to a single agent. For example, the response matrix H for a two sensor array designed to determine that concentration of DMMP as the first agent and Toluene as the second agent is described by the following:

$$H(\Delta f_1, \Delta f_2) = \begin{bmatrix} k_{T_{1,d}} & -\Delta f_1 k_{lt_{1,d}} & k_{T_{1,t}} & -\Delta f_1 k_{lt_{1,t}} \\ k_{T_{2,d}} & -\Delta f_2 k_{lt_{2,d}} & k_{T_{2,t}} & -\Delta f_2 k_{lt_{2,t}} \end{bmatrix} \quad (14)$$

where the parameters $k_{T_{1,d}}$ and $k_{lt_{1,d}}$ characterize the response on the first reagent to DMMP; the parameters $k_{T_{2,d}}$ and $k_{lt_{2,d}}$ characterize the response on the second reagent to DMMP; the parameters $k_{T_{1,t}}$ and $k_{lt_{1,t}}$ characterize the response on the first reagent to Toluene; and the parameters $k_{T2,t}$ and $k_{lt_{2,t}}$ characterize the response on the second reagent to Toluene.

Figure 11:
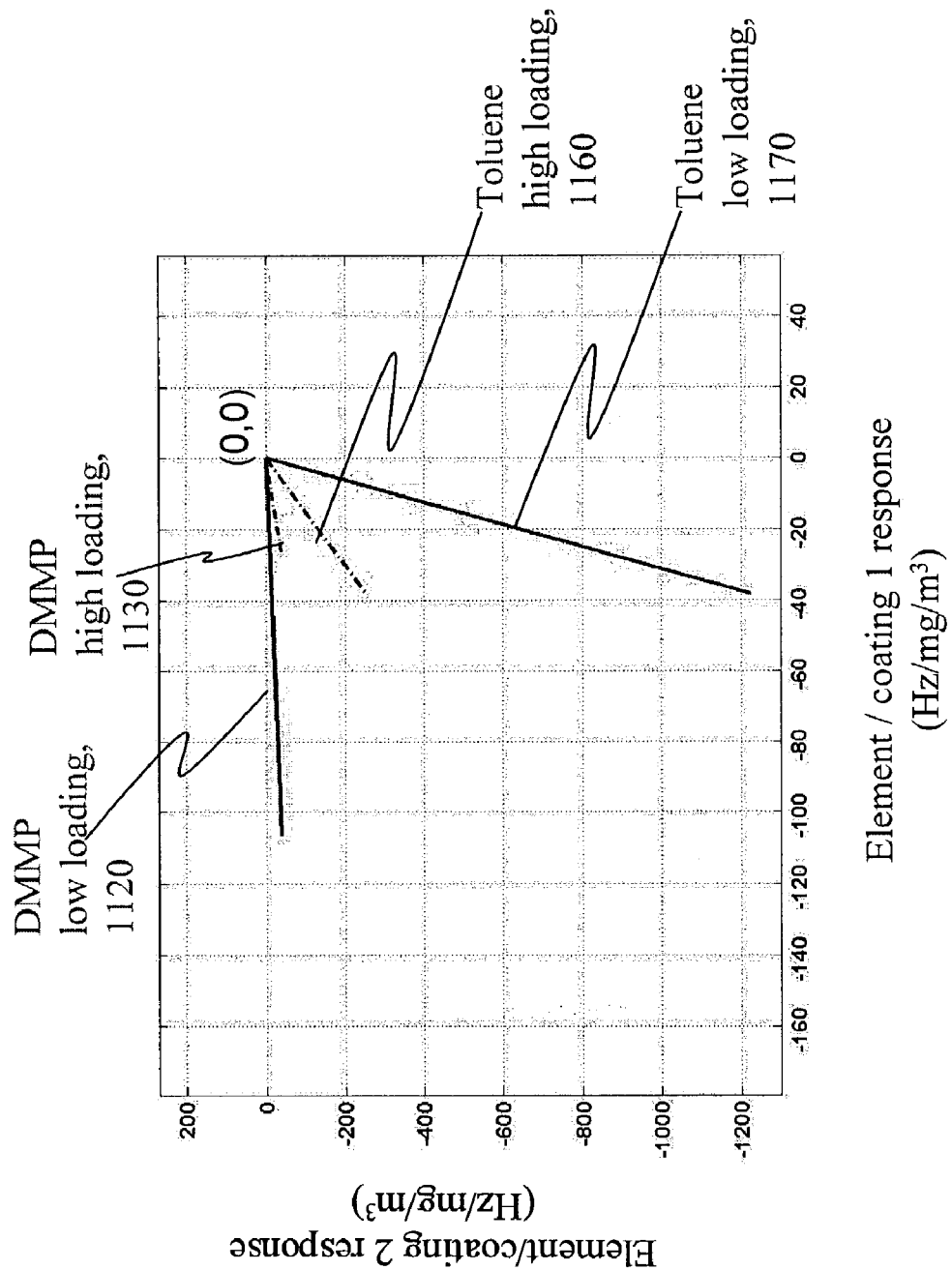
FIG. 11 is a graph depicting the distinct response signatures of two different reagents to two different agents, in accordance with an illustrative embodiment of the invention.

Referring now to FIG. 11, the response signature of two different agents are illustrated graphically with respect to two different reagents. The vertical axis represents the response of a first reagent coating and the horizontal axis represents the response of a second reagent coating. The response signatures of each agent is a nonlinear function of the agent concentration. Each response signature has a magnitude and direction. Line 1120 represents a low loading of DMMP while line 1130 represents a high loading of DMMP. Line 1160 represents a low loading of Toluene while line 1170 represents a high loading of Toluene. These response signatures correspond to the response matrix of equation (14).

As FIG. 11 illustrates, coating 1—the first reagent coating-has a marked response to low concentrations of DMMP and a more subtle response to low concentrations of Toluene. In contrast, coating 2—the second reagent coating-has a marked response to low concentrations of Toluene and a more subtle response to low concentrations of DMMP. Accordingly, if one were selecting an array of sensors to distinguish between DMMP and Toluene, the combination of coating 1 and coating 2 would be a good selection.

FIG. 11 makes an advantage of embodiments of the invention that use a bilinear model evident. In particular, the simplicity of the model allows response signatures to be easily compared and distinguished. The method and system described with respect to FIG. 12 may take advantage of this feature.

Figure 12:
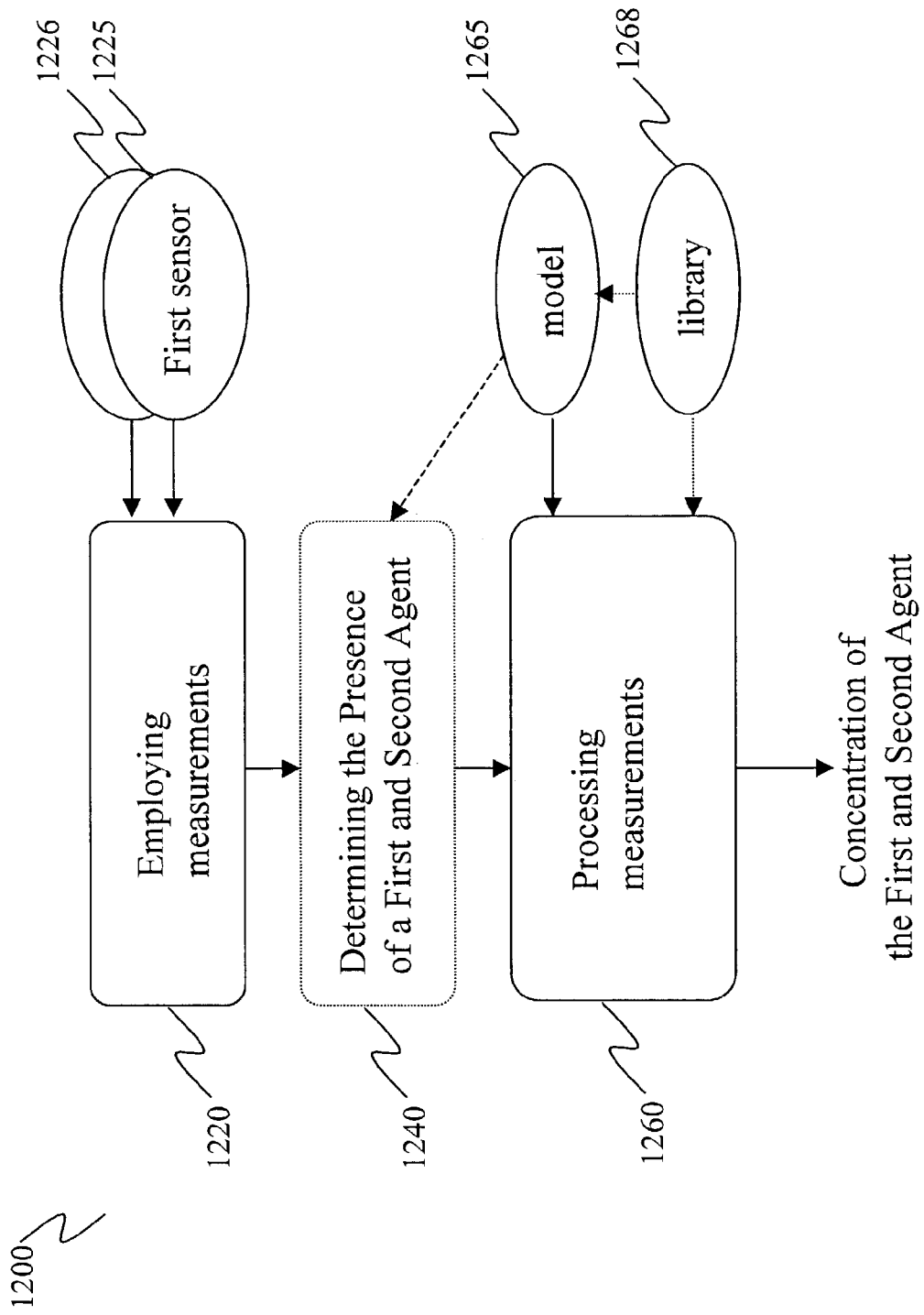
FIG. 12 is a flow diagram depicting a method of determining the concentration of a first agent and the concentration of a second agent in a fluid environment, in accordance with an illustrative embodiment of the invention.

Referring now to FIG. 12, a method 1200 of determining the concentration of two different agents in a fluid environment is described. In step 1220 of the method 1200 of FIG. 12, a plurality of measurements, from a first and a second sensor 1225, 1226, of an attribute that changes in response to the first agent and the second agent are employed. In some illustrative embodiments, each of the sensors 1225, 1226 whose attribute is being measured will comprise a reagent. In such embodiments, the first sensor 1225 will comprise a first reagent while the second sensor 1226 will comprise a second, different reagent. In the illustrative embodiment, each reagent comprises a coating on a flexural plate. The measurements may be taken before the agent/reagent combination reaches a steady-state condition. The measurements may take the form of sensor readings.

In step 1260 of the method 1200 of FIG. 12, the concentration of the first agent and the concentration of the second agent is determined by processing the plurality of measurements using a nonlinear, parametric model of the attribute response 1265. The model 1265 takes the finite capacity of the reagents into account. Parameters characterizing the relevant, individual agent/reagent combinations are incorporated into the model 1265 in one embodiment. In an alternative embodiment, the model 1265 uses parameters characterizing the relevant, individual agent/reagent combinations from a database 1268. The sensor readings are thereby interpreted. In one embodiment, the sensor readings are interpreted in real-time. In an alternative embodiment, the sensor readings are interpreted after being recorded. An exemplary embodiment of step 1260 uses equation (13) and a response matrix such as described in equation (14) to determine the concentration of the first agent and the concentration of the second agent.

Some embodiments of the method illustrated by FIG. 12 include an additional step. In step 1240, the presence of the first agent and the second agent is determined. Such embodiments use the techniques described in the Non-Gaussian Detection patent applications. In the Non-Gaussian Detection techniques, the signal of interest corresponds to sensor attribute measurements associated with the response signature of the first agent. Similarly, one second signal corresponds to sensor attribute measurements associated with the response signature of the second agent. In some such embodiments, step 1240 uses the same model of the attribute response 1265 used in step 1260. In such embodiments, parameters characterizing the relevant, individual agent/ reagent combinations are also used. These parameters are incorporated into the model 1265 in one embodiment and accessed from a database 1268 in an alternative embodiment. The sensor readings are thereby interpreted.

A system to implement the method 1200 of FIG. 12 in some illustrative embodiments comprises a single processor. The processor, in an illustrative embodiment of such a system, determines the concentration of the agent by processing the plurality of measurements using the same model 1265 described with respect to FIG. 12. The processor, in various embodiments, is an electronic component having one or more microprocessors, digital circuitry, and/or analog circuitry to analyze the plurality of measurements. In further embodiments, the processor is part of a computer system. In other embodiments, the processor is a mechanical system, a hydraulic system, a pneumatic system, a chemical system, or any other system or device capable of performing the modeling described with respect to FIG. 12.

In some illustrative embodiments, a system to implement the method 1200 of FIG. 12 may further comprise sensors in signal communication with the processor. Each sensor, in such an embodiment, comprises a reagent and has an attribute that changes in response to the agent. In the illustrative embodiment, the reagent is a coating disposed on the flexural plate of the FPW sensor and the attribute is the vibration frequency. The attribute measurements are communicated to the processor as sensor readings.

In some illustrative embodiments of a system to implement the method 1200 of FIG. 12, the processor incorporates additional functionality to implement Step 1240 of FIG. 12. Alternative embodiments of a system to implement the method of FIG. 12 may further comprise a detector or second processor, such as described in the Non-Gaussian Detection patent applications, to implement Step 1240 of FIG. 12. In these embodiments the detector or second processor is in signal communication with the first processor. The detector or second processor determines the presence of the first and the second agent in the fluid environment.

Finally, in some embodiments of the invention, measurements from a plurality of sensors are employed. The measurements are of a sensor attribute that may change in response to one or more agents. The measurements are processed using a nonlinear, parametric model of an attribute response that takes into account the finite capacity of reagents to determine a plurality of agent concentrations. The plurality of agent concentrations is analyzed to determine if the pattern of the agent concentrations indicates the existence of a condition. It may not be possible to determine the presence of the condition from the measurement of any single sensor attribute. The condition, in one embodiment, is a disease state. In another embodiment, the condition is the presence of a constituent. The analysis is based on a comparison of patterns representing the absence of the condition and one or more patterns representing the presence of the condition.

What is claimed is:

1. A method of determining a concentration of an agent in a fluid environment, the method comprising,
   receiving at least one measurement of an attribute of a sensor immersed in a fluid environment comprising at least one agent, the attribute being based on an interaction of a sensor reagent with the at least one agent;
   providing a nonlinear, parametric model of time-varying dynamics of the interaction between the sensor reagent and the at least one agent, the model accounting for a finite capacity of the sensor reagent to interact with the at least one agent;
   based on the at least one measurement and the model, determining the concentration of the at least one agent in the fluid environment.

2. The method of claim 1, wherein the sensor comprises a vibrating membrane and the attribute comprises a vibration frequency of the vibrating membrane.

3. The method of claim 1, wherein the model represents the time-varying dynamics of an interaction between the sensor reagent and the at least one agent as a bilinear function of the concentration of the agent in the fluid environment.

4. The method of claim 1, wherein the model embraces a plurality of reagent loading modes.

5. The method of claim 1, wherein the at least one agent comprises a biological agent.

6. A system for determining a concentration of an agent in a fluid environment, the system comprising,
   a sensor; and
   a processor in signal communications with the sensor and configured to:
   (a) receive a plurality of measurements of an attribute of a sensor immersed in a fluid environment, the attribute based on an interaction of a sensor reagent with at least one agent in the fluid environment and representing changes of the attribute in response to the at least one agent;
   (b) receive a nonlinear, parametric model of time-varying dynamics of an interaction between the sensor reagent and the at least one agent, the model accounting for a finite capacity of the sensor reagent to interact with the at least one agent; and
   (c) process the plurality of measurements in accordance with the model, thereby determining the concentration of the agent in the fluid environment.

7. The system of claim 6 wherein the sensor further comprises a sensor reagent having a characteristic response to the at least one agent.

8. The system of claim 7, wherein the sensor comprises a plate and a flexure plate wave sensor and the attribute comprises a vibration frequency of the plate sensed by the sensor.

9. The system of claim 6, wherein the sensor reagent is disposed on a surface of the sensor.

10. The system of claim 6, wherein the model further accounts for the stochastic transport of the at least one agent, the stochastic loading of sensor reagents, and the stochastic sensing of sensor reagent loading.

11. A method of determining concentrations of a first agent and a second in a fluid environment, the method comprising,
    receiving from a first sensor and a second sensor, both sensors being immersed in a fluid environment comprising a first agent and a second agent, a plurality of measurements, of an attribute of the sensors that changes in response to the first and second agents;
    receiving a nonlinear, parametric model of time-varying dynamics of the interaction between the sensors and the agents, the model accounting for a finite capacity of the first and second sensors to interact with the first and second agents;
    processing the plurality of measurements using the model; and
    determining the concentrations of the first and second agents in the fluid environment.

12. The method of claim 11 further comprising determining the presence of the first agent and the second agent in the fluid environment.

13. The method of claim 11, wherein the model represents the attribute response as a bilinear function of agent concentration in the fluid environment.

14. The method of claim 11, wherein the model accounts for the stochastic transport of the first and second agents, the stochastic loading of sensor reagents, and the stochastic sensing of sensor reagent loading.

15. The method of claim 11, wherein the model further takes into account a plurality of sensor reagent loading modes.

16. The method of claim 11, wherein the first sensor comprises a vibrating membrane and the attribute comprises a vibration frequency of the vibrating membrane.

17. The method of claim 11, wherein the first sensor comprises a first reagent, and the second sensor comprising a second reagent.

18. The method of claim 17, wherein the first reagent has a first characteristic response to the first agent, the second reagent has a second characteristic response to the first agent, and the first characteristic response is dissimilar to the second characteristic response.

19. A system for determining concentrations of a first agent and a second agent in a fluid environment, the system comprising,
 a processor configured to:
  (a) receive from a first sensor and a second sensor, the sensors being immersed in a fluid environment comprising a first and second agent, a plurality of measurements of an attribute of the sensors that changes in response to the first and second agents;
  (b) receive a non-linear, parametric model of time-varying dynamics of the interaction between the sensors and the agents, the model accounting for a finite capacity of the first and second sensors to interact with the first and second agents;
  (c) process the measurements in accordance with the model; and
  (d) determine the concentrations of the first agent and the second agent in the fluid environment.

20. The system of claim 19 further comprising a first sensor in signal communication with the first processor, wherein the first sensor comprises a first sensor reagent, and a second sensor in signal communication with the first processor, wherein the second sensor comprises a second sensor reagent.

21. The system of claim 20, wherein the first sensor comprises a first plate and a first flexure plate wave sensor, the second sensor comprises a second plate and a second flexure plate wave sensor, and the attribute comprises a vibration frequency of the plates.

22. The system of claim 20, wherein the first reagent has a first characteristic response to the first agent, the second reagent has a second characteristic response to the first agent, and the first characteristic response is dissimilar to the second characteristic response.

23. The system of claim 19, wherein the model represents the attribute response as a bilinear function of agent concentration in the fluid environment.

24. The system of claim 20, wherein the model accounts for the stochastic transport of the agents, the stochastic loading of the sensor reagents, and the stochastic sensing of sensor reagent loading.

25. The system of claim 19 further comprising a second processor in signal communication with the first processor for determining the presence of the first agent and the second agent in the fluid environment.

* * * * *